(12) United States Patent
Ohishi

(10) Patent No.: US 7,751,523 B2
(45) Date of Patent: Jul. 6, 2010

(54) X-RAY DIAGNOSTIC APPARATUS

(75) Inventor: Satoru Ohishi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 19 days.

(21) Appl. No.: 12/174,070

(22) Filed: Jul. 16, 2008

(65) Prior Publication Data

US 2009/0022262 A1 Jan. 22, 2009

(30) Foreign Application Priority Data

Jul. 18, 2007 (JP) ............................... 2007-187427

(51) Int. Cl.
*G01N 23/00* (2006.01)
(52) U.S. Cl. .......................... 378/4; 378/98.12; 382/132
(58) Field of Classification Search ...................... 378/4, 378/91, 98.2, 98.12; 382/131, 132
See application file for complete search history.

(56) References Cited

U.S. PATENT DOCUMENTS

2007/0201609 A1 8/2007 Ohishi et al.

FOREIGN PATENT DOCUMENTS

JP 2007-229473 9/2007

*Primary Examiner*—Jurie Yun
(74) *Attorney, Agent, or Firm*—Oblon, Spivak, McClelland, Maier & Neustadt, L.L.P.

(57) ABSTRACT

An X-ray diagnostic apparatus comprises an X-ray image generating unit which generates a series of a plurality of X-ray images associated with a subject to be examined, a storage unit which stores data of a three-dimensional image associated with the subject, an image processing unit which generates data of a two-dimensional blood vessel image from the stored data of the three-dimensional image, a difference processing unit which generates a plurality of difference images by subtracting the X-ray images from each other, and a display unit which superimposes and displays each of the plurality of difference images and the two-dimensional blood vessel image.

20 Claims, 5 Drawing Sheets

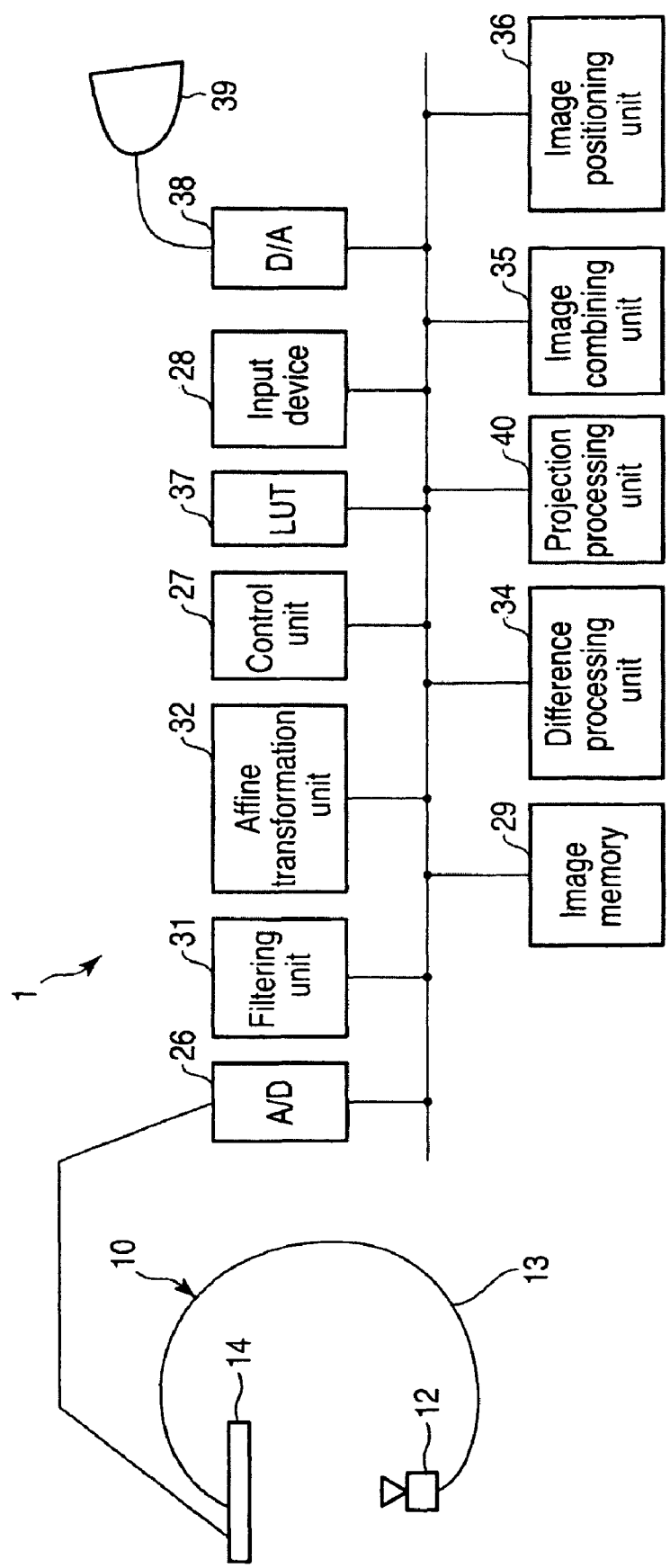
F I G. 1

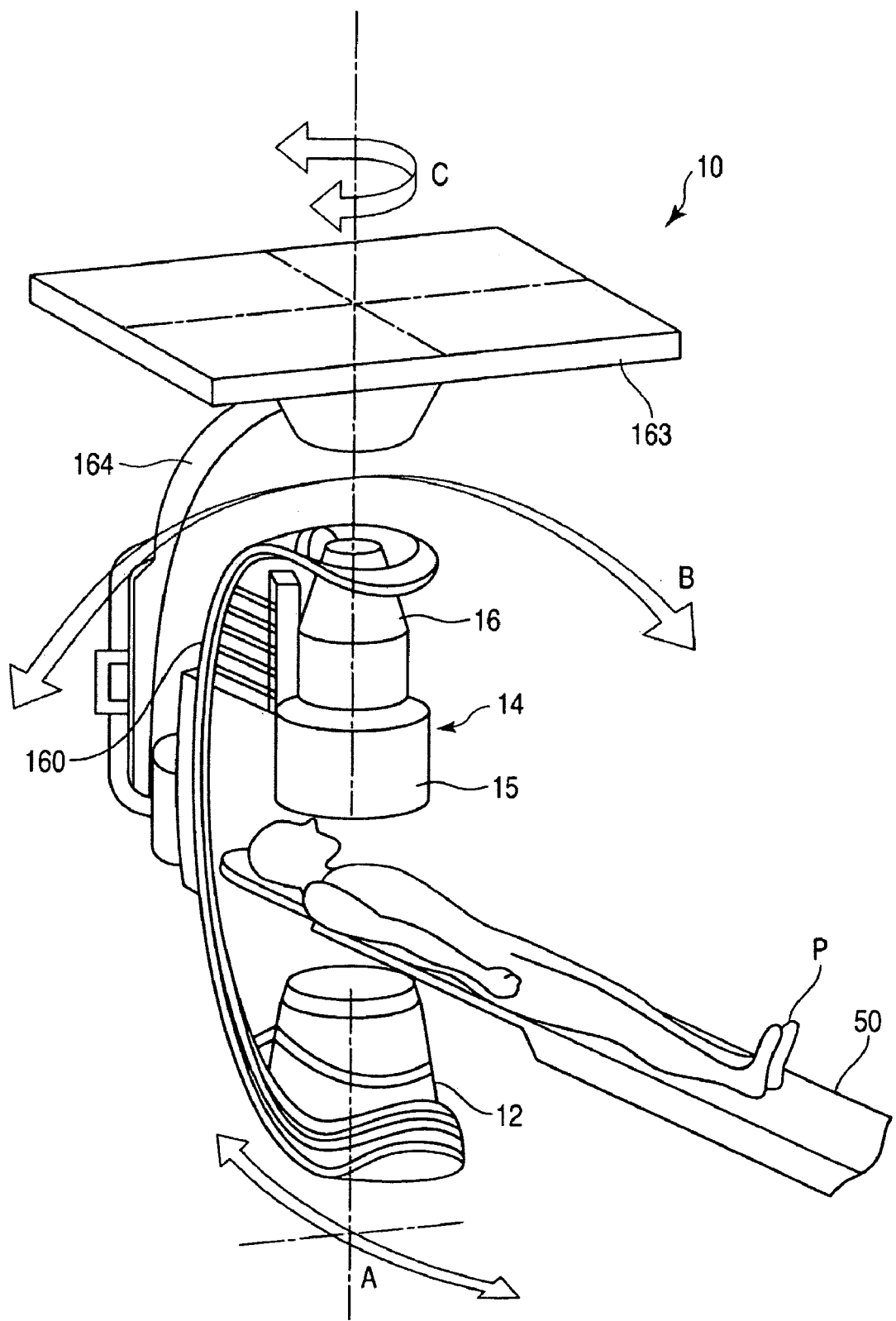
F I G. 2

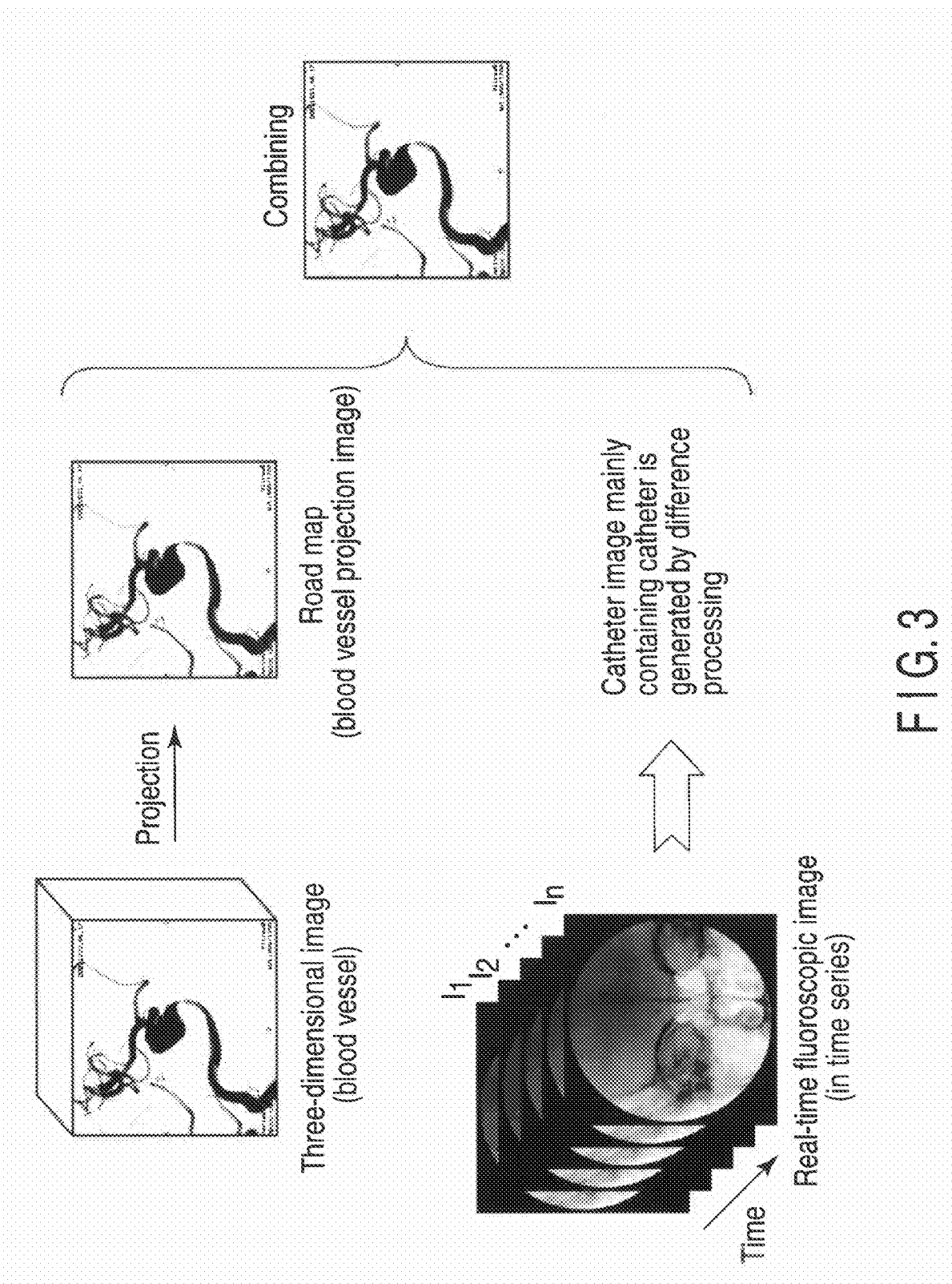
F I G. 3

X-RAY DIAGNOSTIC APPARATUS

CROSS-REFERENCE TO RELATED APPLICATIONS

This application is based upon and claims the benefit of priority from prior Japanese Patent Application No. 2007-187427, filed Jul. 18, 2007, the entire contents of which are incorporated herein by reference.

BACKGROUND OF THE INVENTION

1. Field of the Invention

The present invention relates to an X-ray diagnostic apparatus which displays a road map representing a blood vessel structure.

2. Description of the Related Art

In intervention or angiographic examination, a catheter is inserted into a blood vessel from, for example, the joint of a leg and is brought to a target region through the blood vessel. This catheter or a guide wire inserted in the catheter is moved forward to a target position under fluoroscopic observation of an X-ray image. However, the blood vessel cannot be seen in an X-ray image unless enhanced by a contrast medium. Keeping injecting the contrast medium to visualize the blood vessel may result in renal failure. For this reason, there is available a function of holding an X-ray image of a blood vessel obtained by radiography after a contrast medium is injected once as a two-dimensional road map, and displaying the image upon superimposing it on an X-ray fluoroscopic image obtained in real time. This function allows the operator to discriminate the position of a blood vessel to a certain extent without injecting any contrast medium, and hence is often used especially when a blood vessel structure is complicated and it is difficult to push a catheter or a guide wire into the blood vessel.

When, however, a road map is converted into a three-dimensional image, a portion other than the catheter or guide wire, e.g., a bone, is imaged. This makes it very difficult to see the image of the catheter or guide wire.

BRIEF SUMMARY OF THE INVENTION

It is an object of the present invention to improve the visibility of an image of a catheter or guide wire.

According to an aspect of the present invention, an X-ray diagnostic apparatus comprises: an X-ray image generating unit which generates a series of a plurality of X-ray images associated with a subject to be examined; a storage unit which stores data of a three-dimensional image associated with the subject; an image processing unit which generates data of a two-dimensional blood vessel image from the stored data of the three-dimensional image; a difference processing unit which generates a plurality of difference images by subtracting the X-ray images from each other; and a display unit which superimposes and displays each of the plurality of difference images and the two-dimensional blood vessel image.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an arrangement of an X-ray diagnostic apparatus according to an embodiment of the present invention;

FIG. 2 is a perspective view showing an X-ray imaging mechanism in FIG. 1;

FIG. 3 is a view showing the first processing sequence performed by this embodiment;

DETAILED DESCRIPTION OF THE INVENTION

Figure 4:
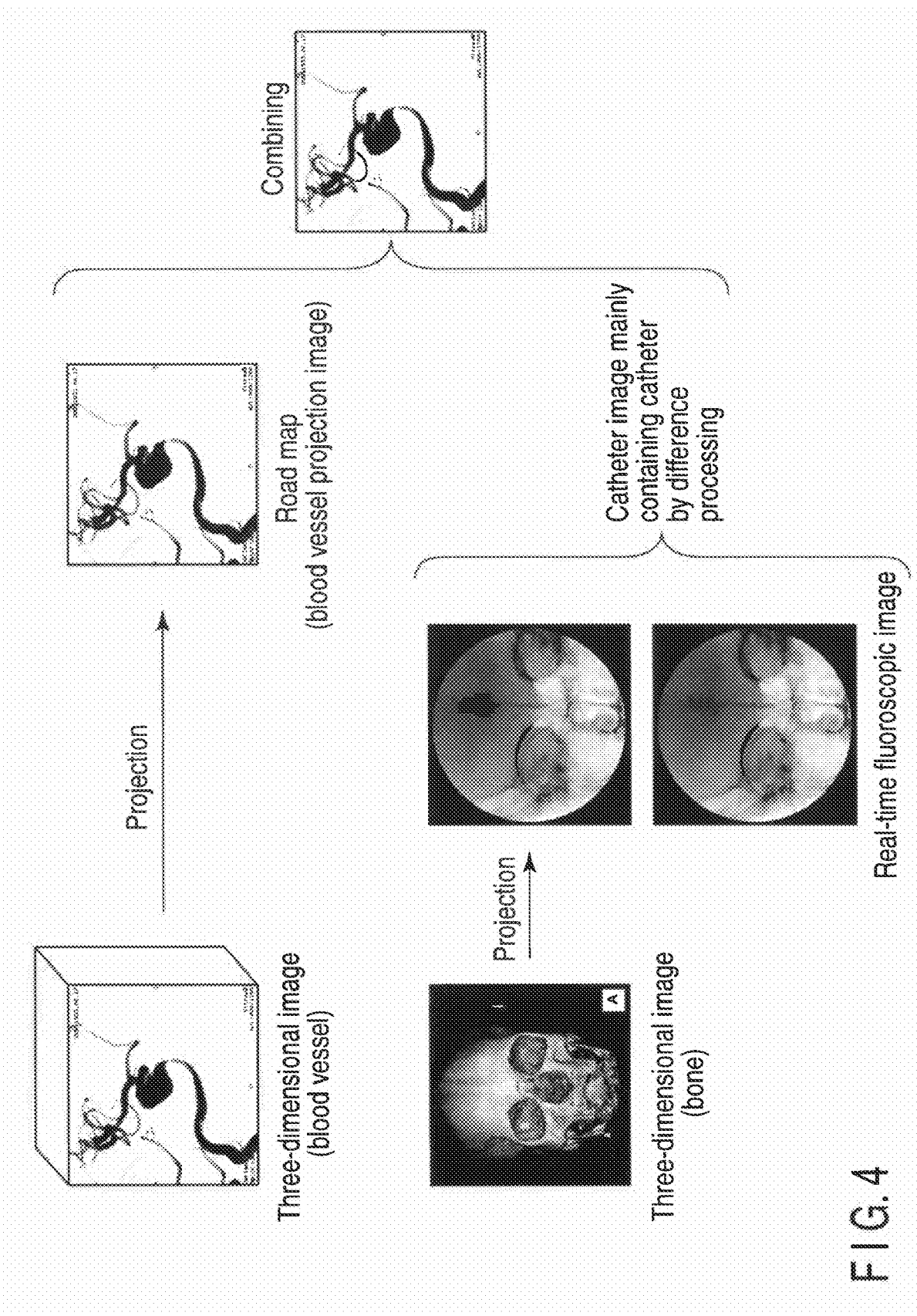
FIG. 4 is a view showing the second processing sequence performed by this embodiment.

An embodiment of the present invention will be described below with reference to the views of the accompanying drawing.

As shown in FIG. 1, an X-ray diagnostic apparatus includes an X-ray imaging mechanism 10 and an image processing apparatus 1. As shown in FIG. 2, the X-ray imaging mechanism 10 includes an X-ray tube 12 and an X-ray detector 14. The X-ray detector 14 comprises a combination of an image intensifier 15 and a TV camera 16. The X-ray detector 14 may comprise a flat panel detector (FPD) having a plurality of semiconductor detection elements arrayed in a matrix form instead of the combination of the image intensifier 15 and the TV camera 16. The X-ray tube 12 is mounted on one end of a C-arm 160. The X-ray detector 14 is mounted on the other end of the C-arm 160 in a direction to face the X-ray tube 12. A subject P on a top 50 of a bed is placed between the X-ray tube 12 and the X-ray detector 14. The C-arm 160 is supported by, for example, a arcuated column 164 suspended from a ceiling base 163. The C-arm 160 is rotatable with respect to three orthogonal axes A, B, and C.

The image processing apparatus 1 is connected to the X-ray detector 14 via an analog/digital converter (A/D) 26. The image processing apparatus 1 comprises the analog/digital converter 26, a control unit 27, an input device 28, an image memory 29, a filtering unit 31 which performs harmonic enhancement filtering or the like, an affine transformation unit 32 which performs image enlargement/movement and the like, a difference processing unit 34, an image combining unit 35, an image positioning unit 36, a lookup table (LUT) 37, a digital/analog converter (D/A) 38, a display 39, and a projection processing unit 40. The input device 28 includes a keyboard and pointing devices such as a mouse.

The image memory 29 stores three-dimensional image data about a target region of a subject to be examined. The three-dimensional image data originates from the X-ray diagnostic apparatus or an X-ray computed tomography apparatus.

The projection processing unit 40 generates three-dimensional blood vessel image data by extracting a blood vessel from the stored three-dimensional image data. The projection processing unit 40 also generates three-dimensional human body image data excluding the blood vessels from the stored three-dimensional image data. The three-dimensional blood vessel image data and the three-dimensional human body image data are stored in the image memory 29, together with the three-dimensional image data.

The projection processing unit 40 generates a blood vessel projection image (to be referred to as a road map hereinafter) from a three-dimensional blood vessel image by projection processing in accordance with a line-of-sight direction and an enlargement ratio on a three-dimensional image coordinate system which are equivalent to the radiographing directions (rotation angles θA, θB, and θC around the rotation axes A, B, and C) and enlargement ratio of the X-ray imaging mechanism 10. The projection processing unit 40 also generates a mask image from a three-dimensional human body image by projection processing in accordance with a line-of-sight direction and an enlargement ratio on the three-dimensional image coordinate system which are equivalent to the radiographing directions (the rotation angles θA, θB, and θC around the rotation axes A, B, and C) and enlargement ratio of the X-ray imaging mechanism 10.

The projection processing unit 40 subtracts X-ray images (fluoroscopic images) from each other, which are obtained by radiography at, for example, a frame rate of 30 frames/sec in time series. As a subtraction target for the latest fluoroscopic image, a fluoroscopic image acquired one frame or a predetermined number of frames before the latest fluoroscopic image is set. However, a subtraction target can be a fluoroscopic image at the beginning of operation of a technique, which is acquired before the insertion of the catheter, or a fluoroscopic image arbitrarily designated by a technician or an operator. With this difference processing, an image of the catheter or guide wire which is displaced upon moving operation is extracted. A difference image obtained by extracting an image of the catheter or guide wire will be referred to as a catheter image hereinafter. The image positioning unit 36 positions a road map and a catheter image with high accuracy via anatomically morphological feature points. The image combining unit 35 cumulatively combines catheter images with the positioned road map. This combined image is displayed on the display 39.

FIG. 3 shows a processing sequence performed by this embodiment. At the start of fluoroscopy, the projection processing unit 40 generates a road map from a three-dimensional blood vessel image in accordance with a line-of-sight direction and an enlargement ratio equivalent to the radiographing directions (the rotation angles θA, θB, and θC around the rotation axes A, B, and C) and enlargement ratio of the X-ray imaging mechanism 10 which are set by the operator. The road map is stored in the image memory 29. When the radiographing direction and the enlargement ratio change during fluoroscopy, a road map is generated again from a three-dimensional blood vessel image in accordance with the radiographing direction and the enlargement ratio after the changes, and is stored in the image memory 29.

With fluoroscopic operation, this apparatus generates a series of X-ray images (fluoroscopic images) at, for example, a frame rate of 30 frames/sec. The apparatus then generates a mask image by adding/averaging fluoroscopic images of a predetermined frames after the start of fluoroscopy. The projection processing unit 40 subtracts the mask image from each fluoroscopic image. With this operation, catheter images are sequentially generated. The image combining unit 35 sequentially superimposes these catheter images on the road map and display the resultant images on the display 39.

With regard to difference processing, the projection processing unit 40 may subtract each of fluoroscopic images obtained by radiography in time series and a fluoroscopic image acquired one frame or a predetermined number of frames before each of the fluoroscopic images in time series to sequentially generate catheter images.

Extracting catheter or guide wire images by difference processing and combining each image with a road map can reduce the deterioration in the visibility of the catheter or guide wire image which is mainly caused by the overlapping of a bone.

The above processing sequence and another processing sequence shown in FIG. 4 can be selectively performed. The processing sequence in FIG. 4 can obtain similar effects. The image memory 29 stores the data of a three-dimensional image containing a bone image which is reconstructed from mask image data before the injection of the contrast medium or the data of a three-dimensional image (three-dimensional bone image) obtained by extracting a human body region from a three-dimensional blood vessel image containing the bone image by threshold processing, together with the data of a blood vessel projection image (road map).

The projection processing unit 40 generates a human body projection image from a three-dimensional human body image by projection processing in accordance with a line-of-sight direction and an enlargement ratio on a three-dimensional image coordinate which are equivalent to the radiographing directions (the rotation angles θA, θB, and θC around the rotation axes A, B, and C) and enlargement ratio of the X-ray imaging mechanism 10, as in the case of the road map.

The projection processing unit 40 sequentially subtracts a human body projection image from each of X-ray images (fluoroscopic images) obtained by radiography at, for example, a frame rate of 30 frames/sec in time series. With this difference processing, an entire catheter or guide wire image is extracted. The image positioning unit 36 positions the difference image (catheter image) obtained by extracting the entire catheter or guide wire image. The image combining unit 35 then sequentially combines each difference image with the road map and displays the resultant image on the display 39.

Extracting a catheter or guide wire image by difference processing and combining it with a road map can reduce the deterioration in the visibility of the catheter or guide wire image which is mainly caused by the overlapping of a bone.

Figure 5:
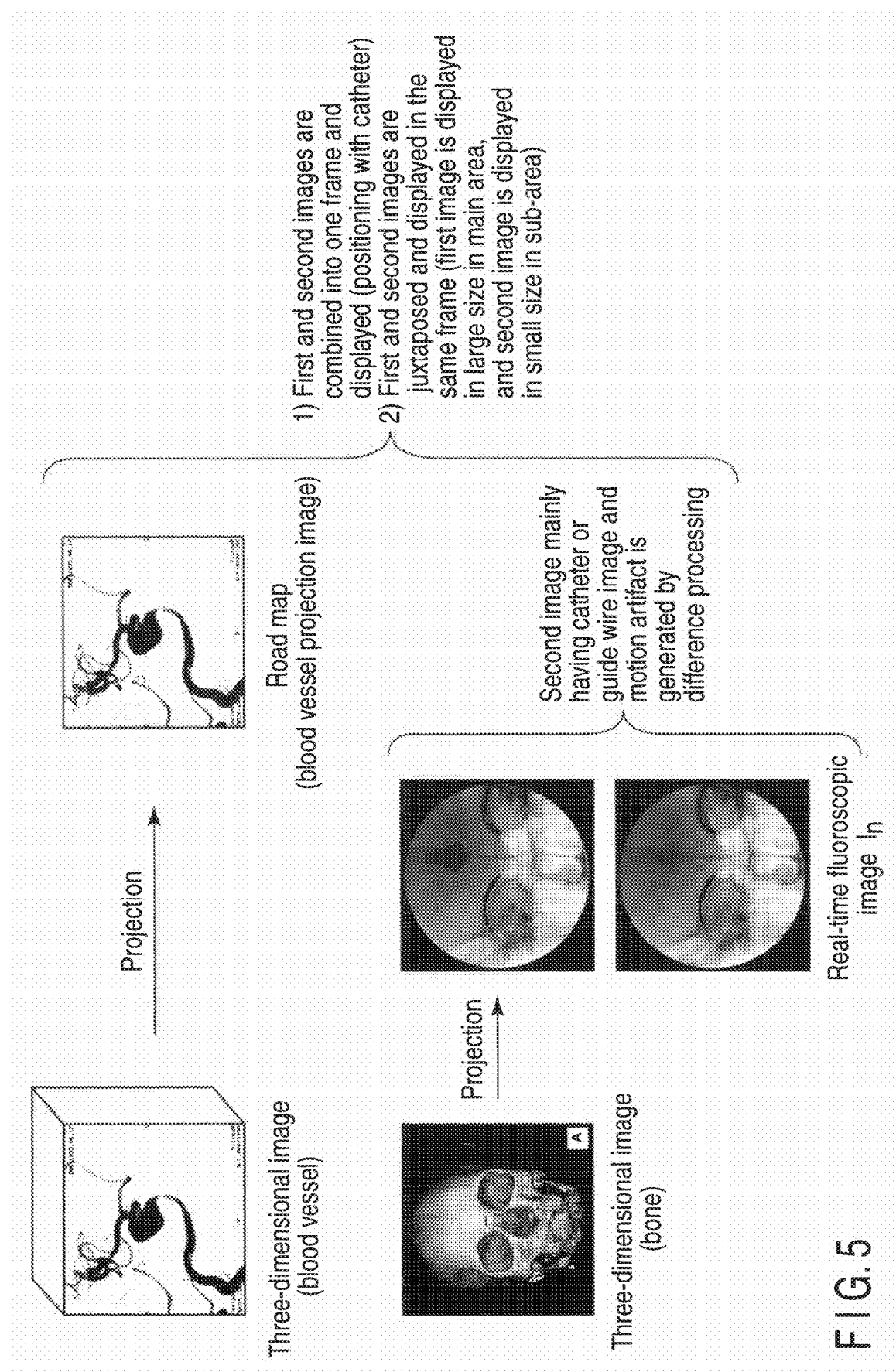
FIG. 5 is a view showing the third processing sequence performed by this embodiment.

As shown in FIG. 5, the control unit 27 displays the composite image in FIG. 3 and the difference image in FIG. 4 upon superimposing or juxtaposing them. When displaying these images upon juxtaposing them, the control unit 27 displays the first difference image in a relatively large size in a main area while displaying the second difference image in a relatively small size in a sub-area. When the subject moves to cause a positional shift in the interval between the instant when three-dimensional image data is generated and the instant when a fluoroscopic image is generated, a region remaining due to the positional shift appears in the second difference image. That is, the second difference image contains positional shift information. The control unit 27 determines whether to display or not display the second difference image, in accordance with the degree of the positional shift of the subject in the interval between the instant when a three-dimensional image is generated and the instant when a fluoroscopic image is generated. The degree of a positional shift can be determined on the basis of the second difference image. For example, the degree of a positional shift can be determined on the basis of one or a combination of the maximum value, median value, average value, and variance of the second difference image. The degree of a positional shift may be determined with reference to the entire region of the second difference image or with reference to a localized part of the second difference image.

Note that the present invention is not limited to the above embodiment, and constituent elements can be variously modified and embodied at the execution stage within the spirit and scope of the invention. Various inventions can be formed by proper combinations of a plurality of constituent elements disclosed in the above embodiments. For example, several constituent elements may be omitted from all the constituent elements in each embodiment. In addition, constituent elements of the different embodiments may be combined as needed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
   an X-ray image generating unit which generates a plurality of X-ray images associated with a subject to be examined;
   a storage unit which stores data of a three-dimensional image associated with the subject;
   an image processing unit which generates data of a two-dimensional blood vessel image from the stored data of the three-dimensional image;
   a difference processing unit which generates a plurality of difference images based on the plurality of X-ray images; and
   a display unit which superimposes and displays each of the plurality of difference images and the two-dimensional blood vessel image.

2. The apparatus according to claim 1, wherein the data of the three-dimensional image originates from one of the X-ray diagnostic apparatus and an X-ray computed tomography apparatus.

3. The apparatus according to claim 1, wherein the plurality of X-ray images are real-time images.

4. The apparatus according to claim 1, wherein the difference processing unit subtracts an averaging image based on several initial X-ray images of the plurality of X-ray images from each of the plurality of X-ray images.

5. The apparatus according to claim 1, wherein the image processing unit projects the stored three-dimensional image in a same direction as a radiographing direction of the plurality of X-ray images to generate the data of the two-dimensional blood vessel image.

6. An X-ray diagnostic apparatus, comprising:
   an X-ray image generating unit which generates a plurality of X-ray images associated with a subject to be examined;
   a storage unit which stores data of a three-dimensional image associated with the subject;
   an image processing unit which generates data of a two-dimensional blood vessel image and data of a two-dimensional human body image from the data of the three-dimensional image;
   a difference processing unit which generates a plurality of difference images by subtracting each of the plurality of X-ray images from the two-dimensional human body image; and
   a display unit which superimposes and displays each of the plurality of difference images and the two-dimensional blood vessel image.

7. The apparatus according to claim 6, wherein the data of the three-dimensional image originates from one of the X-ray diagnostic apparatus and an X-ray computed tomography apparatus.

8. The apparatus according to claim 6, wherein the plurality of X-ray images are real-time images.

9. The apparatus according to claim 6, wherein the image processing unit projects the stored three-dimensional image in a same direction as a radiographing direction of the plurality of X-ray images to generate the data of the second two-dimensional human body image and the data of the two-dimensional blood vessel image.

10. An X-ray diagnostic apparatus, comprising:
    an X-ray image generating unit which generates a plurality of X-ray images associated with a subject to be examined;
    a storage unit which stores data of a three-dimensional image associated with the subject;
    an image processing unit which generates data of a two-dimensional human body image from the data of the three-dimensional image;
    a first difference processing unit which generates a plurality of first difference images based on the plurality of X-ray images;
    an image compositing unit which superimposes the plurality of first difference images on the two-dimensional human body image to obtain composite images;
    a second difference processing unit which generates a plurality of second difference images by subtracting each of the plurality of X-ray images from the two-dimensional human body image; and
    a display unit which displays the composite images and the plurality of second difference images.

11. The apparatus according to claim 10, wherein the data of the three-dimensional image originates from one of the X-ray diagnostic apparatus and an X-ray computed tomography apparatus.

12. The apparatus according to claim 10, wherein the plurality of X-ray images are real-time images.

13. The apparatus according to claim 10, wherein the first difference processing unit subtracts an averaging image based on several initial X-ray images of the plurality of X-ray images from each of the plurality of X-ray images.

14. The apparatus according to claim 10, wherein the image processing unit projects the stored three-dimensional image in a same direction as a radiographing direction of the plurality of X-ray images to generate the data of the two-dimensional human body image.

15. The apparatus according to claim 10, wherein the display unit superimposes and displays the second difference images on the composite images.

16. The apparatus according to claim 10, wherein the display unit displays the composite images in a main area and the second difference images in a sub-area.

17. The apparatus according to claim 10, further comprising a control unit that determines whether to display or not display each second difference image of the plurality of second difference images, in accordance with a degree of a positional shift of the subject in an interval between an instant when the three-dimensional image is generated and an instant when an X-ray image corresponding to the second difference image is generated.

18. The apparatus according to claim 17, wherein the degree of the positional shift is determined on the basis of the second difference image.

19. The apparatus according to claim 18, wherein the degree of the positional shift is determined on the basis of one or a combination of a maximum value, a median value, an average value, and a variance of the second difference image.

20. The apparatus according to claim 19, wherein the degree of the positional shift is determined with reference to a localized part of the second difference image.

* * * * *